(12) United States Patent
Vogt et al.

(10) Patent No.: US 10,875,000 B2
(45) Date of Patent: Dec. 29, 2020

(54) STORAGE AND MIXING DEVICE FOR PRODUCING A BONE CEMENT

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 210 days.

(21) Appl. No.: 15/617,231

(22) Filed: Jun. 8, 2017

(65) Prior Publication Data

US 2017/0354942 A1 Dec. 14, 2017

(30) Foreign Application Priority Data

Jun. 8, 2016 (DE) .................. 10 2016 110 561

(51) Int. Cl.
*B01F 15/02* (2006.01)
*B01F 11/00* (2006.01)
(Continued)

(52) U.S. Cl.
CPC ...... *B01F 15/0258* (2013.01); *A61B 17/8816* (2013.01); *A61B 17/8827* (2013.01);
(Continued)

(58) Field of Classification Search
CPC ............ B01F 15/0258; B01F 15/00506; B01F 15/0087; B01F 15/00974; B01F 15/0206;
(Continued)

(56) References Cited

U.S. PATENT DOCUMENTS

| 4,671,263 A | 6/1987 | Draenert |
| 4,758,096 A | 7/1988 | Gunnarsson |

(Continued)

FOREIGN PATENT DOCUMENTS

| CN | 1163147 A | 10/1997 |
| CN | 101130264 A | 2/2008 |

(Continued)

OTHER PUBLICATIONS

Charnley, J.; "Anchorage of the Femoral Head Prosthesis of the Shalt of the Femur"; The Journal of Bone and Joint Surgery; Feb. 1960, pp. 28-30, vol. 42 B, No. 1, Manchester, England.

(Continued)

*Primary Examiner* — Marc C Howell
(74) *Attorney, Agent, or Firm* — Norris McLaughlin, P.A.

(57) ABSTRACT

A storage and mixing device for PMMA bone cements having a cylindrical interior of the cartridge that is delimited on a front side by a cartridge head with a closed delivery opening, a plunger which is arranged to be axially movable in the cylindrical interior of the cartridge and which is spaced from the cartridge head. The plunger circumferentially rests against the inner wall of the interior, so that the plunger divides the interior of the cartridge into two sections in a gas-tight manner, a powdery first parent component of the bone cement, which is contained in the interior between the plunger and the cartridge head, a feed-through which is arranged in the cartridge head or in the cylinder barrel of the cartridge between the plunger and the cartridge head, wherein the feed-through is connected to a fluid line in which a monomer liquid as a second parent component of the bone cement is contained or into which a monomer liquid is fillable or introducible. A filter is arrangeable in the cartridge head, in the feed-through and/or in the fluid line, wherein the filter is permeable to the monomer liquid and (Continued)

impermeable to the first parent component, wherein the plunger is spaced from a back side of the cylindrical interior, located opposite the front side, to an extent that, by moving the plunger in the direction of the back side, a reduced pressure is producible in the interior of the cartridge between the plunger and the cartridge head, wherein the reduced pressure is able to suck the monomer liquid out of the fluid line into the interior of the cartridge.

25 Claims, 8 Drawing Sheets

(51) Int. Cl.
| | |
|---|---|
| *B01F 15/00* | (2006.01) |
| *A61B 17/88* | (2006.01) |
| *B01F 3/12* | (2006.01) |
| *B01F 3/14* | (2006.01) |
| *B01F 7/00* | (2006.01) |
| *B01F 7/16* | (2006.01) |

(52) U.S. Cl.
CPC ........ *A61B 17/8833* (2013.01); *B01F 3/1221* (2013.01); *B01F 3/14* (2013.01); *B01F 7/007* (2013.01); *B01F 7/161* (2013.01); *B01F 11/0054* (2013.01); *B01F 15/0087* (2013.01); *B01F 15/00506* (2013.01); *B01F 15/00974* (2013.01); *B01F 15/0206* (2013.01); *B01F 15/0237* (2013.01); *A61B 2017/8838* (2013.01); *B01F 2215/0029* (2013.01)

(58) Field of Classification Search
CPC ............... B01F 15/0237; B01F 3/1221; A61B 17/8816; A61B 17/8827; A61B 17/8833
USPC ............................................................ 366/6
See application file for complete search history.

(56) References Cited

U.S. PATENT DOCUMENTS

| | | | |
|---|---|---|---|
| 4,973,168 A | 11/1990 | Chan | |
| 5,100,241 A | 3/1992 | Chan | |
| 5,344,232 A | 9/1994 | Nelson et al. | |
| 5,551,778 A | 9/1996 | Hauke et al. | |
| 5,586,821 A | 12/1996 | Bonitati et al. | |
| 5,588,745 A | 12/1996 | Tanaka et al. | |
| 5,624,184 A | 4/1997 | Chan | |
| 5,997,544 A | 12/1999 | Nies et al. | |
| 6,017,349 A * | 1/2000 | Heller ................ A61B 17/8827 366/139 |
| 6,033,105 A | 3/2000 | Barker et al. | |
| 6,709,149 B1 * | 3/2004 | Tepic ..................... A61L 24/06 366/139 |
| 7,959,349 B2 | 6/2011 | Sattig et al. | |
| 8,757,866 B2 | 6/2014 | Vogt et al. | |
| 9,019,586 B2 | 4/2015 | Vogt et al. | |
| 9,339,317 B2 | 5/2016 | Vogt et al. | |
| 10,059,479 B2 | 8/2018 | Vogt et al. | |
| 10,307,508 B2 | 6/2019 | Vogt | |
| 2007/0217282 A1 | 9/2007 | Lidgren et al. | |
| 2008/0037365 A1* | 2/2008 | Axelsson ............... B01F 13/06 366/163.1 |
| 2008/0304355 A1 | 12/2008 | Sattig et al. | |
| 2010/0329074 A1* | 12/2010 | Vogt ................... A61B 17/8825 366/190 |
| 2012/0155214 A1* | 6/2012 | Faccioli ............ A61B 17/8825 366/130 |
| 2013/0182528 A1 | 7/2013 | Vogt et al. | |
| 2014/0098629 A1* | 4/2014 | Greter ................ B01F 11/0054 366/184 |
| 2014/0126320 A1 | 5/2014 | Vogt | |
| 2015/0164568 A1 | 6/2015 | Vogt | |
| 2015/0367301 A1 | 12/2015 | Vogt et al. | |

FOREIGN PATENT DOCUMENTS

| | | |
|---|---|---|
| CN | 102120156 A | 7/2011 |
| CN | 102551871 A | 7/2012 |
| CN | 103189019 A | 7/2013 |
| CN | 103619457 A | 3/2014 |
| CN | 103801216 A | 5/2014 |
| CN | 104707519 A | 6/2015 |
| CN | 105268359 A | 1/2016 |
| DE | 3 640 279 A1 | 6/1987 |
| DE | 69812726 T2 | 2/2004 |
| DE | 10 2007 026 034 A1 | 12/2008 |
| DE | 10 2009 031 178 B3 | 9/2010 |
| DE | 10 2010 046 055 A1 | 3/2012 |
| DE | 10 2014 108 569 B3 | 10/2015 |
| EP | 0 692 229 A1 | 1/1996 |
| EP | 0796653 A2 | 9/1997 |
| EP | 1 005 901 A2 | 6/2000 |
| EP | 1 016 452 A2 | 7/2000 |
| EP | 1 020 167 A2 | 7/2000 |
| EP | 1886647 A1 | 2/2008 |
| WO | 94/26403 A1 | 11/1994 |
| WO | 99/67015 A1 | 12/1999 |
| WO | 00/35506 A1 | 6/2000 |
| WO | 2012/174670 A1 | 12/2012 |

OTHER PUBLICATIONS

Chinese Office Action dated Dec. 23, 2019, in connection with Chinese Patent Application No. 201710426917.1.

* cited by examiner

STORAGE AND MIXING DEVICE FOR PRODUCING A BONE CEMENT

This application claims foreign priority benefit under 35 U.S.C. 119 of German Application No. DE 10 2016 110 561.9 filed Jun. 8, 2016.

DESCRIPTION

The invention relates to a storage and mixing device for two-component polymethyl methacrylate bone cements, said storage and mixing device having a cartridge with a cylindrical interior.

The invention also relates to a method for mixing parent components of a bone cement, in particular a two-component polymethyl methacrylate bone cement, using such a storage and mixing device.

Polymethyl methacrylate (PMMA) bone cements can be traced back to the fundamental work of Sir Charnley (Charnley, J.: Anchorage of the femoral head prosthesis of the shaft of the femur. J. Bone Joint Surg. 42 (1960) 28-30). PMMA bone cements consist of a liquid monomer component and a powder component. The monomer component generally contains the methyl methacrylate monomer and an activator (N,N-dimethyl-p-toluidine) dissolved therein. The powder component, also known as bone cement powder, includes one or more polymers, which are produced on the basis of methyl methacrylate and comonomers, such as styrene, methyl acrylate or similar monomers, by polymerization, preferably suspension polymerization, an X-ray-opaque material and the initiator dibenzoyl peroxide. When mixing the powder component with the monomer component, a plastically deformable paste, the actual bone cement, which is usually known as bone cement paste, is obtained as a result of the polymers of the powder component swelling in the methyl methacrylate. When mixing the powder component with the monomer component, the N,N-dimethyl-p-toluidine activator reacts with dibenzoyl peroxide, forming radicals. The radicals formed initiate the radical polymerization of methyl methacrylate. As the polymerization of methyl methacrylate continues, the viscosity of the bone cement paste increases until said paste solidifies.

The monomer most frequently used in polymethyl methacrylate bone cements is methyl methacrylate. Redox initiator systems usually consist of peroxides, accelerators and, if required, suitable reducing agents. Radicals are only formed when all elements of the redox initiator systems interact. For this reason, the elements of the redox initiator system are arranged in the separate parent components in such a manner that these cannot trigger a radical polymerization. If the composition is suitable, the parent components are storage-stable. It is only when the two parent components are mixed to form a cement paste that the elements of the redox initiator system, which were previously stored separately in the two pastes, liquids or powders, react, forming radicals which trigger the radical polymerization of the at least one monomer. The radical polymerization then leads to the formation of polymers, using the monomer, while the cement paste hardens.

PMMA bone cements can be mixed in suitable mixing receptacles with the aid of spatulas, by mixing the cement powder with the monomer liquid. Here, air bubbles can be trapped in the bone cement paste, which may negatively affect the mechanical properties of the hardened bone cement.

To avoid air inclusions in the bone cement paste, a plurality of vacuum cementing systems have been described, of which the following are listed as examples: U.S. Pat. Nos. 6,033,105 A, 5,624,184 A, 4,671,263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, U.S. Pat. No. 5,344,232 A. The above vacuum cementing systems require an external vacuum pump to be connected in order to produce the reduced pressure. These are generally operated with compressed air using the Venturi principle. The compressed air required to operate the vacuum pumps is obtained either from stationary compressed air facilities or from electrically actuated compressors. In addition, it is also possible to use electrically actuated vacuum pumps to produce the vacuum.

A further development in cementing technology includes cementing systems in which both the cement powder and the monomer liquid are already packaged in separate compartments of the mixing systems and are only mixed together in the cementing system directly before the cement application. Such closed full-prepacked mixing systems have been proposed in EP 692 229 A1, DE 10 2009 31 178 B3, U.S. Pat. Nos. 5,997,544 A, 6,709,149 B1, DE 698 12 726 T2 and U.S. Pat. No. 5,588,745 A. These mixing systems require an external vacuum source too. From EP 0 796 653 A2, a device for producing bone cement from a bone cement powder and a monomer liquid in a cartridge is known, in which a vacuum is drawn by means of a connectable vacuum plunger. The disadvantage of this system is that, after a monomer liquid container has been opened or connected, monomer liquid can already penetrate into the bone cement powder and react before the remaining monomer liquid is sucked into the cartridge by means of the vacuum plunger. As a result, hardened pieces of bone cement can form in the cement paste, making it inhomogeneous, which complicates applicability of the bone cement paste and negatively affects the mechanical properties of the hardened bone cement. In addition, the use of the device is relatively complex and therefore prone to error due to the numerous steps involved in connecting the parts of the device and producing the vacuum.

The U.S. Pat. No. 8,757,866 B2 discloses a storage and mixing device as a full-prepacked mixing system, in which the parent components required for producing the bone cement paste are already stored in the storage and mixing device and can be combined and mixed in the storage and mixing device. The storage and mixing device has a two-piece delivery plunger for closing a cement cartridge. Here, a combination of a gas-permeable sterilization plunger and a gas-impermeable sealing plunger is used. This principle of a closed vacuum mixing system is realized in the closed PALACOS® PRO cementing system, which is produced and distributed by Heraeus Medical GmbH.

WO 2012/174670 A1 discloses a device for mixing and delivering a product with few bubbles, in which the parent components are filled into a chamber for mixing. Gases are to be pressed out of the mixture by means of a spring. The disadvantage is that the device is not suitable for storing the parent components.

WO 00/35506 A1 proposes a device in which polymethyl methacrylate bone cement powder is stored in a cartridge, wherein the cement powder fills the entire volume of the cartridge and the intermediate spaces between the particles of the cement powder have a volume that corresponds to the volume of the monomer liquid required for producing bone cement paste with the cement powder stored in the cartridge. This device is structured in such a manner that a vacuum causes the monomer liquid to be introduced into the cartridge from above, wherein, for this purpose, a vacuum is applied at a vacuum port on the underside of the cartridge. As a result, the monomer liquid is drawn through the cement powder while the air located in the intermediate spaces of the cement particles is displaced by the monomer liquid. Here, the cement paste formed is not mechanically mixed with a stirrer.

The disadvantage of this system is that cement powders which swell quickly with the monomer liquid cannot be mixed with this device, as the quickly swelling cement powder particles form a gel-type barrier after the monomer liquid has penetrated into the cement powder up to approximately 1 to 2 cm and hinder the migration of the monomer liquid through the entire cement powder. Further, the possibility cannot be excluded that a vacuum causes the monomer liquid to be sucked off via the vacuum port after the monomer liquid has completely penetrated the cement powder. Then, insufficient monomer liquid is available for hardening by radical polymerization, or the mixing ratio, and therefore also the consistency of the bone cement, is inadvertently altered. Further, it is a problem that the air trapped between the cement powder particles is to be displaced from above downwards by the monomer liquid, as the air, which is specifically lighter than the monomer liquid, has the desire to wander upwards in the cement powder due to gravity, rather than migrating downwards in the direction of the vacuum port.

When vacuum mixing systems are used for cementing, external vacuum pumps must be provided. These vacuum pumps are expensive and must be cleaned after use. Further, vacuum hoses are required to connect the vacuum pumps to the vacuum mixing systems. These vacuum hoses must be provided with the vacuum mixing systems. Before mixing with a vacuum mixing system, the vacuum pump must therefore first be assembled in the operating theater (OP theater) and connected to an energy source, such as compressed air or electric power. The vacuum pump is then connected to the vacuum mixing system by means of a vacuum hose. These assembly steps cost valuable OP time and are open to possible error. The vacuum pump and the connecting lines to the vacuum mixing system and to external energy sources and supply lines require space and present potential stumbling hazards and obstacles, which may interfere with the occasionally hectic procedure during an operation.

An interesting concept is proposed by EP 1 886 647 A1. Here, the cement powder is stored in an evacuated cartridge, and the monomer liquid is located in a separate container. When the cartridge, which is under reduced pressure, is opened, the monomer liquid is sucked into the cartridge without air flowing in. A bone cement paste is produced which is free of air inclusions. This concept requires that the cartridge remains closed to be vacuum-tight during storage before use, and no non-sterile air can enter. For this purpose, the cartridge must be hermetically sealed in a stable manner. The disadvantage is therefore that the structure is complex and that the contents of the cartridge cannot be mixed by means of a mixing system to be operated externally after the monomer liquid has been sucked in, as a feed-through for a mixing rod or a mixing tube cannot easily be rendered permanently vacuum-tight.

The object of the invention is therefore to overcome the disadvantages of the prior art. In particular, the disadvantages of the known vacuum mixing systems with an external vacuum source are to be overcome. Here, the invention has the object, among others, to develop a simple closed storage and mixing device in which polymethyl methacrylate bone cement powder (cement powder) and monomer liquid are stored in separate compartments and can then be mixed. The medical user should be able to combine and mix the polymethyl methacrylate bone cement powder with the monomer liquid within the storage and mixing device without the two parent components coming into contact with the medical user. Any contact of the medical user with the polymethyl methacrylate bone cement powder and with the monomer liquid should be excluded as far as possible. The device to be developed is preferably a full-prepacked mixing system. The storage and mixing device should be designed in such a manner that the monomer liquid can be transferred into the polymethyl methacrylate bone cement powder without the use of external vacuum pumps which are actuated by compressed air or compressors. It is further important that the storage and mixing device ensures, in a functional and reliable manner, the production of bone cement paste without external energy sources, such as compressed air, vacuum or electric power, even under the simplest external conditions. The storage and mixing device should be usable autonomously without additional technical equipment. Also, the storage and mixing device should be structured as simply and inexpensively as possible.

The storage and mixing device should be simplified such that, with just one manual operating element, a monomer liquid container or a glass ampoule or a foil bag as a monomer liquid container can first be opened, and then, without using an externally produced vacuum, a transfer of the monomer liquid into the cartridge with the cement powder contained therein can be performed manually. Faulty operation should be precluded as far as possible by the construction.

A method should further be provided, which enables a monomer liquid transfer as well as mixing in full-prepacked mixing systems and in which, after the monomer liquid container has been opened, only a single operating element must be operated to transfer the monomer liquid, produce a reduced pressure in the mixing chamber (the cartridge) and mix with the bone cement powder to form the desired bone cement paste. Here, it should be possible to produce the storage and mixing device to be developed mainly from inexpensive plastic.

Further, a storage and mixing device which can be produced at low cost and which functions reliably for mixing a medical bone cement and for storing the parent components of the bone cement as well as a method for mixing the bone cement should be found, in which the simplest possible manual operation for mixing the parent components can be used, as far as possible without the necessity of using an external or additional energy source and without air inclusions being formed in the mixed product.

The first parent component of the polymethyl methacrylate bone cement as a mixed product should be a powder or bone cement powder, and the second parent component should be present in the form of a liquid, the monomer liquid. It should preferably be possible to store the two parent components of the bone cement separately in the full-prepacked mixing system and to securely combine them using the storage and mixing device.

The objects of the invention are achieved by a storage and mixing device for two-component polymethyl methacrylate bone cements, said storage and mixing device having a cartridge with a cylindrical interior, wherein the cylindrical interior is delimited on a front side by a cartridge head with a closed delivery opening, a plunger which is arranged to be axially movable in the cylindrical interior of the cartridge and which is spaced from the cartridge head, wherein the plunger circumferentially rests against the inner wall of the interior, so that the plunger divides the interior of the cartridge into two sections in a gas-tight manner, a powdery first parent component of the bone cement, which is contained in the interior between the plunger and the cartridge head, a feed-through which is arranged in the cartridge head or in the cylinder barrel of the cartridge between the plunger and the cartridge head, wherein the feed-through is connected to a fluid line in which a monomer liquid as a second parent component of the bone cement is contained or into which a monomer liquid is fillable or introducible, a filter which is arranged in the cartridge head, in the feed-through and/or in the fluid line, wherein the filter is permeable to the monomer liquid and impermeable to the first parent component, wherein the plunger is spaced from a back side of the cylindrical interior, located opposite the front side, to an extent that, by moving the plunger in the direction of the back side, a reduced pressure is producible in the interior of the cartridge between the plunger and the cartridge head, wherein the reduced pressure is able to suck the monomer liquid out of the fluid line into the interior of the cartridge.

It can preferably be provided that the first parent component is a cement powder.

The interior of the cartridge has a cylindrical geometry. The cylindrical shape is the simplest with which the interior of the cartridge can be realized. In geometric terms, a cylindrical shape is the shape of a general cylinder with any base area, i.e. not only a cylinder with a circular base. The delimiting inner wall of the interior can therefore be a cylinder with any base, and the cylinder barrel of the cartridge, if present, can also be a cylinder with any base, i.e. also with a non-circular or non-round base. According to the invention, however, a cylindrical geometry with a rotationally symmetrical and in particular a circular base is preferred for the interior of the cartridge as these are easiest to produce and it is less easy for the plunger to get stuck in the interior when it is axially moved in the interior. In addition, there is less probability of possible leaks between the inner wall of the interior and the plunger during movement of the plunger.

The fact that the plunger is axially movable in the cylindrical interior of the cartridge means that the plunger is axially movable along the cylinder axis of the cylindrical interior.

Preferably, no further structural element is provided between the plunger and the powdery first parent component. The back side of the interior is also the back side of the cartridge.

The filter must strictly prevent the powdery first parent component and also dusts of the first parent component from making their way forward as otherwise the powder will block the fluid line within a short time when the monomer liquid comes into contact with the first parent component, thus making the storage and mixing device unsuitable for use, i.e. monomer liquid cannot be transferred into the cartridge any more.

In the storage and mixing device according to the invention it can be provided that the plunger in the interior of the cartridge is pushable or pullable manually in the direction of the back side of the interior by means of a rod or another force transmission means, so that a reduced pressure is produced in the interior of the cartridge between the plunger and the cartridge head, wherein preferably an actuating means or a handle for operating the rod or the force transmission means is affixed to the rod or the force transmission means.

In this way, the reduced pressure can be produced manually in a simple and direct manner, which reduces the risk of possible malfunctions on the one hand and avoids complex and expensive structural elements, such as motors, energy stores or controls, on the other. In addition, this can ensure simple and safe operability of the storage and mixing device.

It can further be provided that the filter is a porous filter. Preferably it can also be provided that the filter is impermeable to cement powder.

According to the invention, the filter and in particular the porous filter prevents cement powder or the powdery first parent component from making its way into the fluid line as far as the monomer liquid, prematurely reacting there with the monomer liquid, solidifying or gelling, and blocking the fluid line as a result. For this purpose, the filter is preferably arranged in the cartridge head, in the feed-through or in the fluid line in the region of the feed-through.

According to the invention, it is preferably provided that the plunger is spaced from the back side of the cylindrical interior such (or to an extent) that the space for displacement of the plunger to reach the back side is at least equal to the volume of the monomer liquid to be sucked in, preferably at least equal to the volume of the fluid line and a monomer liquid container in which the monomer liquid is contained.

This ensures that the reduced pressure to be produced in the interior of the cartridge is sufficient to suck the desired quantity of the monomer liquid into the interior of the cartridge.

In a further development of the storage and mixing device according to the invention it can also be provided that the storage and mixing device has a container which is separate from the cartridge and in which the monomer liquid is contained, wherein the container is connected or connectable to the fluid line, wherein preferably a closed glass ampoule containing the monomer liquid is arranged or is arrangeable in the container, wherein the glass ampoule is breakable open within the container.

In this way, a so-called full-prepacked mixing system is provided in which all parent components, i.e. the two parent components (cement powder as the first parent component and monomer liquid as the second parent component), are already contained in the storage and mixing device, can be stored therein and are mixable within the storage and mixing device.

According to the invention, it can be provided that the storage and mixing device has openings through which air flows into the fluid line from outside. Here, in storage and mixing devices with a container according to the invention it can be provided that the openings are arranged in the container for the monomer liquid, particularly preferably in a lid on the back side of the container.

In this way, air can flow into the fluid line from outside, and therefore the monomer liquid need not be sucked into the cartridge against a vacuum or a reduced pressure. As a result, the transfer of the monomer liquid into the cartridge is made easier.

Here, it can be provided that the cartridge, the separate container and the fluid line are connected to a common stand, wherein the container and the fluid line are permanently connected to the stand and the cartridge is releasably connected to the stand, the cartridge preferably being screwed to the stand by means of a thread or connected to the stand by means of a latching mechanism.

This simplifies the use of the storage and mixing device. In operation theaters, a planar surface, such as a table, is present in most cases, so that the storage and mixing device can be installed and used there with the aid of the stand, without a need to hold the storage and mixing device in the hand. This simplifies the use of the storage and mixing device even further.

It can further be provided that a monomer liquid container, in particular a foil bag or a glass ampoule, is contained in the separate container and is openable within the separate container, so that the monomer liquid flows out of the opened monomer liquid container into the fluid line, wherein preferably an opening device for opening the monomer liquid container, which is operable from outside, is arranged on the container.

In this way, a so-called full-prepacked mixing system is provided in which all parent components, i.e. the two parent components (cement powder as the first powdery parent component and monomer liquid as the second parent component), are already contained in the storage and mixing device, are storable therein and are mixable within the storage and mixing device. The glass ampoule or the foil bag, which is preferably coated with aluminum, are particularly suitable for long-term storage of the monomer liquid as the second parent component for producing the PMMA bone cement paste. This simplifies and facilitates the use of the storage and mixing device.

In order for the monomer liquid to be able to flow without the influence of additional force, the storage and mixing device must be correctly installed, so that gravity produces the desired direction of flow. Accordingly, the terms "at the top" and "at the bottom" used within the context of the present invention, as well as "above" and "below" are always in relation to the correct installation of the storage and mixing device.

A monomer liquid container with several chambers for storing the monomer liquid can also be used. Within the context of the present invention, a monomer liquid container is therefore also understood as being a plurality of separate, individual partial monomer liquid containers which are introducible into the separate container and are openable by means of the opening device.

It can be provided that a screen or a filter is arranged in or on the fluid line to the cartridge, with which fragments or scraps of the opened monomer liquid container can be retained. The screen or filter is preferably located in the container, directly below the monomer liquid container.

A further development of the invention relating to the use of gravity as an actuating means for the flow of monomer liquid into the fluid line proposes that the separate container for the monomer liquid container is arranged above the fluid line to the cartridge. As a result, the monomer liquid can flow out of the monomer liquid container into the fluid line due to gravity after the monomer liquid container has been opened.

According to a particularly preferred further development of the present invention it can be provided that a mixing device is arranged in the interior of the cartridge between the plunger and the cartridge head, by means of which the first parent component is mixable with the monomer liquid in the interior of the cartridge.

In this way, the first parent component can be well mixed with the monomer liquid in the interior of the cartridge in order to produce a bone cement paste which is as homogeneous as possible. The mixing device can preferably be operated manually from outside.

In storage and mixing devices with a mixing device it can be provided that the mixing device is operable from outside the cartridge by means of a mixing rod, wherein the mixing rod passes through the cartridge head in a gas-tight manner and is rotatable and movable in the axial direction, the mixing rod preferably passing through the delivery opening.

In this way, the mixing device can be operated manually from outside the storage and mixing device in a simple and powerful manner. In addition, the user can make a good estimation of the consistency of the bone cement paste and therefore the usability of the bone cement paste, based on the resistance against movement of the mixing device.

According to the invention, it can be provided that a fastening means, in particular an outer thread, is provided in the region of the cartridge head on the outside of the cartridge. A separate delivery pipe is affixable thereto. Preferably however, a hollow tubular mixing rod is used, by means of which the mixing device is operable and the plunger in the interior is pushable in the direction of the back side of the interior in order to produce the reduced pressure in the interior, wherein the tubular mixing rod can be used as a delivery pipe after a closure has been removed from the tubular mixing rod. In this case, an outer thread is not required any more, although the outer thread can also be used to affix the cartridge in a delivery device or press-out device for advancement of the plunger in the direction of the cartridge head in order to press out and apply the ready-mixed bone cement paste. To close the delivery opening, an extractable core is arranged within the hollow mixing rod, which closes the tubular mixing rod to the outside.

It can further be provided that the plunger is pushable in the direction of the back side of the interior of the cartridge by means of the mixing rod.

In this way, the plunger can be actuated by means of the same device which is used for actuating the mixing device, namely the mixing rod, in order to produce the reduced pressure in the interior of the cartridge. As a result, only one common device is required for both functions, and the storage and mixing device requires only one feed-through that must be sealed to serve both purposes.

A further development of the present invention proposes that the mixing rod is a delivery pipe in which a manually removable core is arranged, so that the mixed bone cement paste is dischargeable from the interior of the cartridge through the delivery pipe without the core.

For this purpose, the delivery pipe is pulled out of the interior of the cartridge as far as a stop, preferably in advance. If the mixing rod is used as a delivery pipe, no additional or separate delivery pipe is required which would have to be affixed to the storage and mixing device. The mixing rod is guided in or passes through the delivery opening for this purpose while being sealed against the cartridge head and being axially movable and rotatable.

Alternatively it can be provided that the storage and mixing device has a separate delivery pipe with a static mixer, which is affixable to the cartridge, preferably to the fastening means on the cartridge, wherein particularly preferably an inner thread matching the outer thread on the cartridge is provided on the delivery pipe and/or elements of a bayonet mount and/or latching elements of a latching mechanism are provided.

It can also be provided that in the interior of the cartridge, on the back side, a stop is provided which delimits movement of the plunger in the direction of the back side.

This prevents the plunger from being able to be displaced beyond the back side of the interior and bone cement paste from inadvertently passing to the outside.

It can further be provided that the plunger has at least one latching element which is releasably engageable with a complementary latching element on the inner side of the cartridge in the region of the back side of the interior.

In this way, the plunger is held in position when it has been moved as far as the back side. This prevents inadvertent movement of the plunger while mixing the contents of the interior and movement of the plunger beyond the latching position. To deliver the ready-mixed bone cement paste, the latching mechanism can be easily released.

In storage and mixing devices according to the invention it can be provided that the cartridge, the cartridge head and the plunger are made of plastic, wherein preferred plastics are polyethylene-co-vinyl alcohol (EVOH), polybutylene terephthalate (PBT), polyethylene terephthalate (PET) and polymethacrylic acid methyl ester co-acrylonitrile.

According to the invention, it can further be provided that a gas-permeable opening, in particular a closable gas-permeable opening, is arranged in the cartridge head, wherein a porous disc which is permeable to gases and impermeable to solid particles is arranged between the first parent component and the opening, wherein the porous disc is preferably arranged in the cartridge head.

In this way, a sterilization of the storage and mixing device can also be performed in the interior of the cartridge with the aid of a sterilizing gas, such as ethylene oxide. The opening is preferably arranged next to the delivery opening and is closable by means of a closure.

It can be provided that an opening is arranged in the cartridge head, above the porous disc, which opening is closable to be gas-tight and has an area of at least 20 mm$^2$ and is connected to the surrounding atmosphere.

To avoid inadvertently filling the interior of the cartridge with monomer liquid, it can be provided that the fluid line has an upwardly pointing loop, wherein the highest point of the loop is located above a reservoir for the monomer liquid or above the connection between the separate container and a widened part of the fluid line.

In this way, the monomer liquid can be prevented from passing straight away into the interior of the cartridge when it is filled into the fluid line. This inverted U-shaped loop of the fluid line achieves the situation that, before the plunger is moved in the direction of the back side of the interior of the cartridge, the monomer liquid in the fluid line remains in the fluid line up to the height of the vertex, which prevents premature admission of the monomer liquid to the cement powder. With high-viscosity cements in particular, premature contact of even small quantities of the monomer liquid with the cement powder can lead to clogging of the fluid line. The fluid line can be transparent or translucent, so that the user can visually check the monomer liquid transfer. For this purpose, in particular, a viewing window can be provided in the storage and mixing device, through which the loop with the highest vertex can be seen.

According to the invention, it can be provided that the plunger is a delivery plunger by means of which the mixed bone cement paste is pressable out of the cartridge through the delivery opening or through the delivery pipe or the hollow mixing rod by advancing the delivery plunger in the direction of the cartridge head.

Preferably, the cartridge head is arranged at the top and the back side of the cartridge is arranged at the bottom when the storage and mixing device is installed correctly.

The objects addressed by the present invention are also achieved by a method for mixing the parent components of a bone cement, in particular a multicomponent polymethyl methacrylate bone cement, using a storage and mixing device according to the invention, characterized by the following steps:
a) the filter prevents the first parent component from making its way into the fluid line,
b) the plunger is moved in the direction of the back side of the cylindrical interior of the cartridge, wherein a reduced pressure is produced in the interior of the cartridge between the plunger and the cartridge head due to said movement of the plunger,
c) the monomer liquid is sucked out of the fluid line and through the filter into the interior of the cartridge by the reduced pressure in the interior,
d) the monomer liquid and the first parent component are mixed to form the bone cement paste in the interior of the cartridge, and
e) the bone cement paste is discharged from the interior of the cartridge through the opened delivery opening by advancing the plunger in the direction of the cartridge head.

Steps a), b) and c) can, at least at times, be performed simultaneously, while steps d) and e) are performed chronologically after each other and also chronologically after steps b) and c). Step a) relates to an effect of the filter which, strictly speaking, continues throughout the method as a whole but must be present at least at the beginning of the method. As a reduced pressure is already building up in the interior of the cartridge during the aforesaid movement, this reduced pressure can already cause the monomer liquid to be sucked into the interior of the cartridge.

It can be provided that (seen over time) the monomer liquid is introduced into the fluid line before step b), in particular after a monomer liquid container has been opened in the storage and mixing device.

In this way, the method becomes usable for full-prepacked systems as the monomer liquid can also be stored in the storage and mixing device, in a dedicated monomer liquid container, such as a glass ampoule or a metallized foil bag, for longer periods.

In the method according to the invention it can also be provided that, in step b), the plunger is pressed in the direction of the back side of the cartridge by means of a mixing rod, wherein the mixing rod is movably supported in a gas-tight feed-through in the cartridge head, and, in step d), the monomer liquid is mixed with the first parent component by moving a mixing device, which is connected to the mixing rod, in the interior of the cartridge between the plunger and the cartridge head, by moving the mixing rod and therefore the mixing device. The gas-tight feed-through is preferably realized by the delivery opening.

In this way, the mixing rod, which is present for moving the mixing device in the interior of the cartridge, is also used for moving the plunger and hence for producing the reduced pressure in the interior of the cartridge. Particularly preferably, this mixing rod can be designed as a tube and therefore also be used as a delivery pipe for applying the mixed bone cement paste.

Here, it can again be provided that the mixing device is drawn towards the cartridge head by means of the mixing rod and a core is removed from the mixing rod between steps d) and e), so that the mixing rod without the core forms a delivery pipe through which the mixed bone cement paste is pressed out of the interior of the cartridge in step e).

In this way, the mixing rod becomes also usable as a delivery pipe, and the delivery opening is usable to pass the mixing rod therethrough.

Within the context of the present invention, it is further proposed that, before step e), the cartridge is separated from the storage and mixing device and is inserted into a press-out device by means of which the plunger is pressed in the direction of the cartridge head in step e), using a tappet or an advanceable rod, in order to discharge the bone cement paste from the interior of the cartridge.

In this way, the cartridge can be used separately from the storage and mixing device in order to apply the ready-mixed bone cement paste. This facilitates handling during application.

It can further be provided that the cartridge head is closed to be gas-tight before step b).

This ensures that a reduced pressure is producible in the interior of the cartridge, which is used to suck in the monomer liquid. At the same time, however, the interior of the cartridge can first be sterilized with the aid of a sterilizing gas, such as ethylene oxide, through the opened cartridge head.

It can also be provided that air flows in from outside the storage and mixing device through openings in a container for the monomer liquid in step c).

This prevents the situation that the sucking-in of the monomer liquid into the cartridge is hindered or complicated due to a reduced pressure building up in the container for the monomer liquid.

Storage and mixing devices according to the invention and methods according to the invention can, in theory, also be realized using a plurality of cartridges in each of which a movable plunger for producing a reduced pressure is arranged. Such solutions are understood as being within the scope of the present invention as, here too, just one cartridge is operated or is operatable individually according to the invention.

The invention is based on the surprising recognition that the plunger, which is also used to deliver the mixed bone cement paste from the cartridge, can first be used to produce a reduced pressure and to suck in the monomer liquid. If the mixing rod is also used to operate or move the plunger in order to produce the reduced pressure, additional structural elements can be avoided here. Further, the mixing rod can also be used as a delivery pipe in order to minimize the number of structural elements required. Here, the idea is that the plunger at first does not rest against the back side of the interior of the cartridge but is spaced from it. The stroke of the plunger to reach the back side of the interior of the cartridge can then be used to produce a reduced pressure in the interior of the cartridge by which the monomer liquid can be sucked into the interior of the cartridge. The remaining reduced pressure, if any, can then be used to mix the parent components together under reduced pressure, so that as few gas or air inclusions as possible will form in the bone cement paste being produced.

A storage and mixing device for polymethyl methacrylate bone cement according to the invention is, for example, composed of a) a cylindrical cartridge,
b) a plunger which is axially movable in the cylindrical cartridge,
c) a cartridge head with a feed-through for a mixing rod,
d) a mixing rod which is axially displaceable through the feed-through of the cartridge head,
e) a mixing device which is connected to the end of the mixing rod arranged in the interior of the cartridge,
f) an actuating means which is arranged at the outer end of the mixing rod,
g) at least one monomer liquid container arranged outside the cartridge,
h) an opening device for the monomer liquid container,
i) a fluid line which provides a liquid-permeable connection of the at least one monomer liquid container with the cavity formed by the cartridge, the cartridge head and the plunger,
j) a cement powder which is arranged in the cavity formed by the cartridge, the cartridge head and the plunger,
k) wherein the plunger is axially arranged in the cartridge in such a manner that the space for displacement formed by the cartridge, the cartridge base and the plunger has a volume equal to or larger than the total volume of the fluid line and the at least one monomer liquid container.

The feed-through for the mixing rod is realized by the delivery opening, or is called such herein when the mixing rod is used as a delivery pipe. The actuating means can, for example, be a handle by means of which the mixing rod is manually operable.

According to the invention, a foot part can be provided here, to which the cartridge is releasably connected and which is permanently connected to the at least one monomer liquid container.

It can further be provided that a porous disc is arranged in the cartridge head, which disc is permeable to gases and liquids and is connected to a gas-permeable feed-through and closes the cavity, allowing gases and liquids and not allowing solid particles to pass.

An opening can be arranged in the cartridge head, above the porous disc, which opening is closable to be gas-tight and has an area of at least 20 mm$^2$ and is connected to the surrounding atmosphere.

According to the invention, it can further be provided that the plunger has at least one latching element which can be releasably engaged with a complementary latching element on the inner side of the cartridge above the cartridge base.

The invention includes, for example, a method for mixing and delivering polymethyl methacrylate bone cement. Said method is characterized by the following sequential steps:

a) closing the cartridge head to be gas-tight,
b) opening the at least one monomer liquid container,
c) pressing the actuating means of the mixing rod in the direction of the cartridge base (back side of the interior of the cartridge),
d) displacing the plunger in the direction of the cartridge base by means of the mixing rod,
e) producing a reduced pressure in the cavity (in the interior of the cartridge) formed by the cartridge, the cartridge head and the plunger,
f) transferring the monomer liquid from the opened monomer liquid container through the fluid line into the cavity by said reduced pressure,
g) mixing the cement powder with the monomer liquid by manually actuating the actuating element of the mixing rod by axial and rotating movement of the mixing device,
h) drawing the mixing rod towards the cartridge head,
i) removing a core from the hollow mixing rod,
j) inserting the cartridge into a press-out device,
k) actuating the press-out device, wherein the plunger is moved in the direction of the cartridge head, and
l) pressing the mixed bone cement paste out of the cartridge through the hollow mixing rod.

Another embodiment of the invention will be explained below with reference to eight schematic figures, without limiting the invention in any way however. The figures show:

FIG. 5: a schematic cross-sectional view of the storage and mixing device where the monomer liquid has been sucked in;

Figure 1:
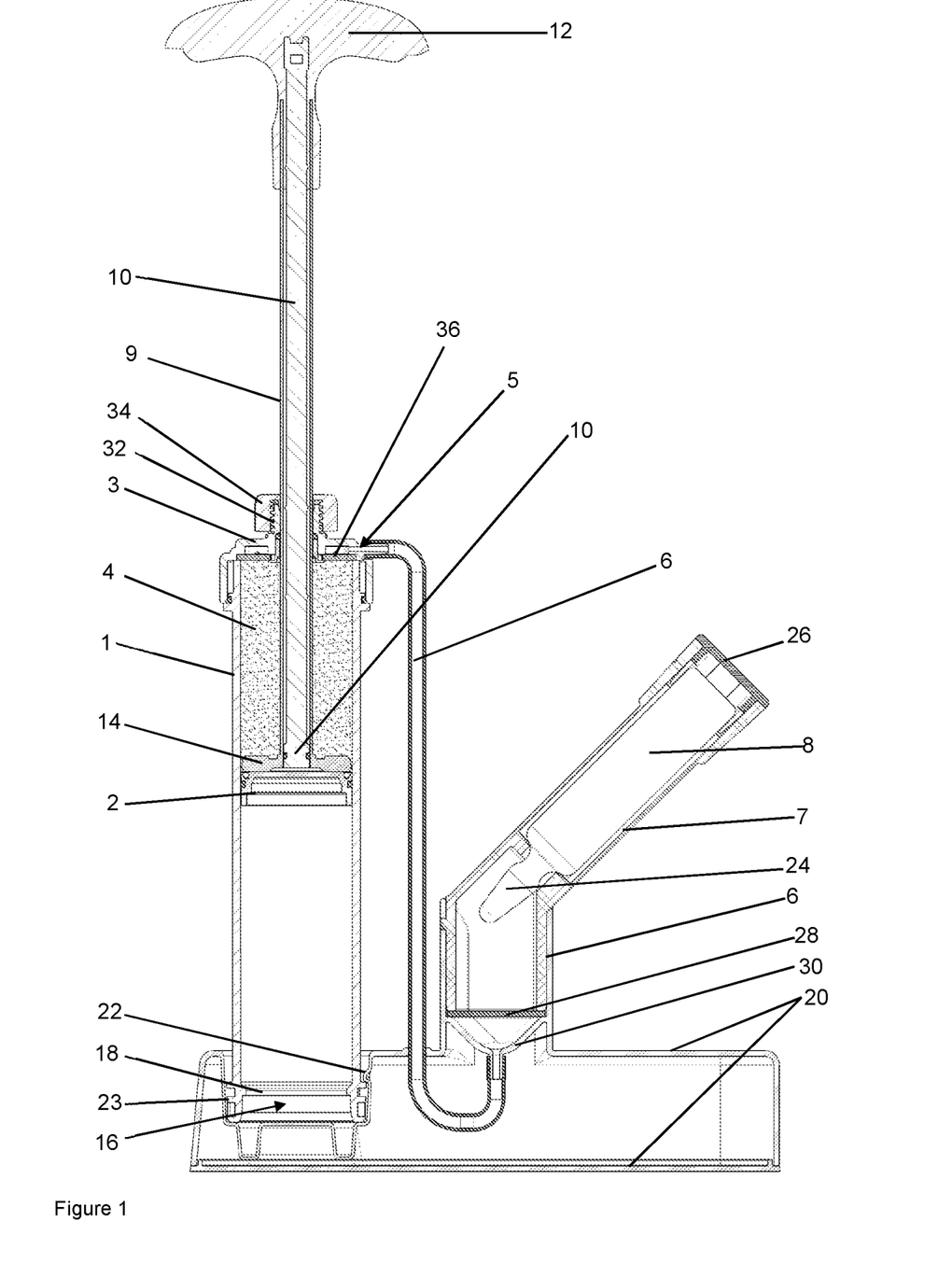
FIG. 1: a schematic cross-sectional view of an exemplary storage and mixing device according to the invention in the initial state.

The figures show an exemplary embodiment of a storage and mixing device according to the invention. Here, FIG. 1 shows a schematic cross-sectional view of the exemplary storage and mixing device according to the invention in the initial state. The storage and mixing device comprises a cartridge 1 with a cylindrical interior in which a plunger 2 is arranged to be linearly movable in the axial direction. On the front side, the interior or the cartridge 1 is closed by a cartridge head 3 similar to a lid or a cap. The cartridge head 3 is sealed against the cartridge 1 by means of a circumferential seal. In the interior of the cartridge 1, a bone cement powder 4 as the first parent component 4 of a PMMA bone cement is located between the plunger 2 and the cartridge head 3.

The plunger 2 is in gas-tight contact with the inner wall of the interior of the cartridge 1 by means of a circumferential rubber seal. In this way, movement of the plunger 2 away from the cartridge head 3 can cause a reduced pressure to be produced in the interior of the cartridge 1, which is passed on to a fluid line 6 through a feed-through 5 in the cartridge head 3 or acts on the fluid line 6. The fluid line 6 first extends downwards, parallel to the axis of the cylindrical cartridge 1, away from the cartridge head 3, then makes a loop and continues in the opposite direction, upwards, where the fluid line 6 widens. The widened part of the fluid line 6 is arranged below a container 7, which is separate from the cartridge 1 and into which a glass ampoule 8 is inserted upside down. The glass ampoule 8 is not shown in section in the sectional views of FIGS. 1 and 3 to 6, and is filled with a monomer liquid 42 (see FIGS. 3 to 6) in FIG. 1. The widened fluid line 6 forms a receptacle for the monomer liquid 42 from the glass ampoule 8.

A central delivery opening is located in the cartridge head 3, with a hollow or tubular mixing rod 9 passing therethrough. The hollow mixing rod 9 is closed inside by means of a core 10 which can be pulled out of the mixing rod 9. In the region of the delivery opening, the mixing rod 9 is sealed against the cartridge head 3 by means of a circumferential seal, so that the reduced pressure in the interior of the cartridge 1 cannot (or at least not so quickly) draw air between the cartridge head 3 and the mixing rod 9 into the interior of the cartridge 1, even when the mixing rod 9 is rotated and moved in the longitudinal direction in the delivery opening.

A handle 12 is arranged on the front end of the mixing rod 9, by means of which the mixing rod 9 can be manually moved in the longitudinal direction relative to the cartridge 1 and can be axially rotated. In addition, the handle 12 can be used to pull the core 10 out of the mixing rod 9 after a latching mechanism (not shown) has been released or a resistance has been overcome.

A mixing device 14 with a number of mixing blades 14 is affixed to the mixing rod 9 in the interior of the cartridge 1 between the plunger 2 and the cartridge head 3, so that the mixing device 14 will rotate and move axially in the interior of the cartridge 1 when the mixing rod 9 is rotated and moved relative to the cartridge 1. In this way, the contents in the interior of the cartridge 1 can be mechanically mixed with the aid of the mixing device 14 by means of the mixing rod 9.

To produce a reduced pressure in the interior of the cartridge 1, the plunger 2 can be moved in the direction of a back side 16 of the cartridge 1 (at the bottom, i.e. downwards in FIGS. 1 to 7) or in the direction of the back side 16 of the interior of the cartridge 1, by manually pressing the plunger 2 in the direction of the back side 16 with the aid of the mixing rod 9. To prevent the plunger 2 from being able to be pressed out of the interior of the cartridge 1 at the bottom, a stop 18 in the form of a circumferential bead is provided on the inner side of the cartridge 1 in the region of the back side 16. The plunger 2 can therefore only be pressed as far as the stop 18 in the direction of the back side 16 of the cartridge 1 (see FIGS. 5 and 6).

The cartridge 1 is releasably connected to a foot part 20. For this purpose, the cartridge 1 is engaged with the foot part 20 by means of a latching nose 22 at the bottom, i.e. in the region of the back side 16. Two circumferential projections 23 are arranged on the outside of the back side 16 of the cartridge 1 for this purpose. These projections 23 can also be used to affix a press-out device (not shown) by means of which the ready-mixed bone cement paste 44 (see FIG. 6) can be applied.

The glass ampoule 8 has a breakable ampoule head 24. When the ampoule head 24 is broken off of broken open, the glass ampoule 8 will be opened. The container 7 is made of an elastically deformable material which has a thickening on the neck between the ampoule head 24 and the body of the ampoule 8. In this way, the ampoule head 24 is securely supported, while the body of the ampoule 8 can be moved due to the elasticity of the insert that forms the container 7. The glass ampoule 8 can therefore be broken open within the storage and mixing device. On the back side of the container 7, a plug 26 is provided as a lid 26 by means of which the glass ampoule 8 is held in position.

A filter 28 and/or screen 28 is arranged in the widened region of the fluid line 6 below the container 7 (i.e. in the monomer liquid receptacle), which keeps back fragments or glass splinters of the glass ampoule 8 which may be produced when the glass ampoule 8 is broken open. Below the filter 28 and/or screen 28, the fluid line 6 tapers via a funnel 30 by means of which the monomer liquid 42 (see FIGS. 2 to 6) is guided into the thin region of the fluid line 6.

A fitting 32 with an outer thread is provided on the cartridge head 3 in the region of the delivery opening. A conical sleeve nut 34 can be screwed onto this outer thread as a fastening device 34 in order to fix the mixing rod 9 relative to the cartridge head 3. To be able to fix the mixing rod 9 relative to the cartridge head 3, the sleeve nut 34 is screwed further onto the outer thread of the fitting 32. To prevent this at first or to avoid inadvertent fixation, an extractable securing device (not shown) in the form of a buckle with a gripping tab can be provided, which is arranged between the sleeve nut 34 and the cartridge head 3. When the securing device is drawn off, the sleeve nut 34 can be screwed further onto the outer thread of the fitting 32, so that the fitting 32 is compressed, thus fixing the mixing rod 9 relative to the cartridge head 3.

An additional lateral opening is provided in the cartridge head 3, through which the interior of the cartridge 1 is accessible by sterilizing gases, such as ethylene oxide. As shown, the lateral opening is closed by means of a closure 40.

A porous disc 36 or a porous filter 36 is arranged between the cartridge head 3 and the interior of the cartridge 1, which disc or filter is permeable to gases and liquids but impermeable to powders and solid materials, such as the bone cement powder 4, so that the feed-through 5 is connected to the remaining interior of the cartridge 1 only via the porous filter 36. The porous filter 36 prevents the bone cement powder 4 from making its way into the fluid line 6, and therefore an inadvertent premature reaction of the bone cement powder 4 with the monomer liquid 42 (see FIGS. 2 to 6) and hence an inadvertent blocking of the thin part of the fluid line 6.

Figure 2:
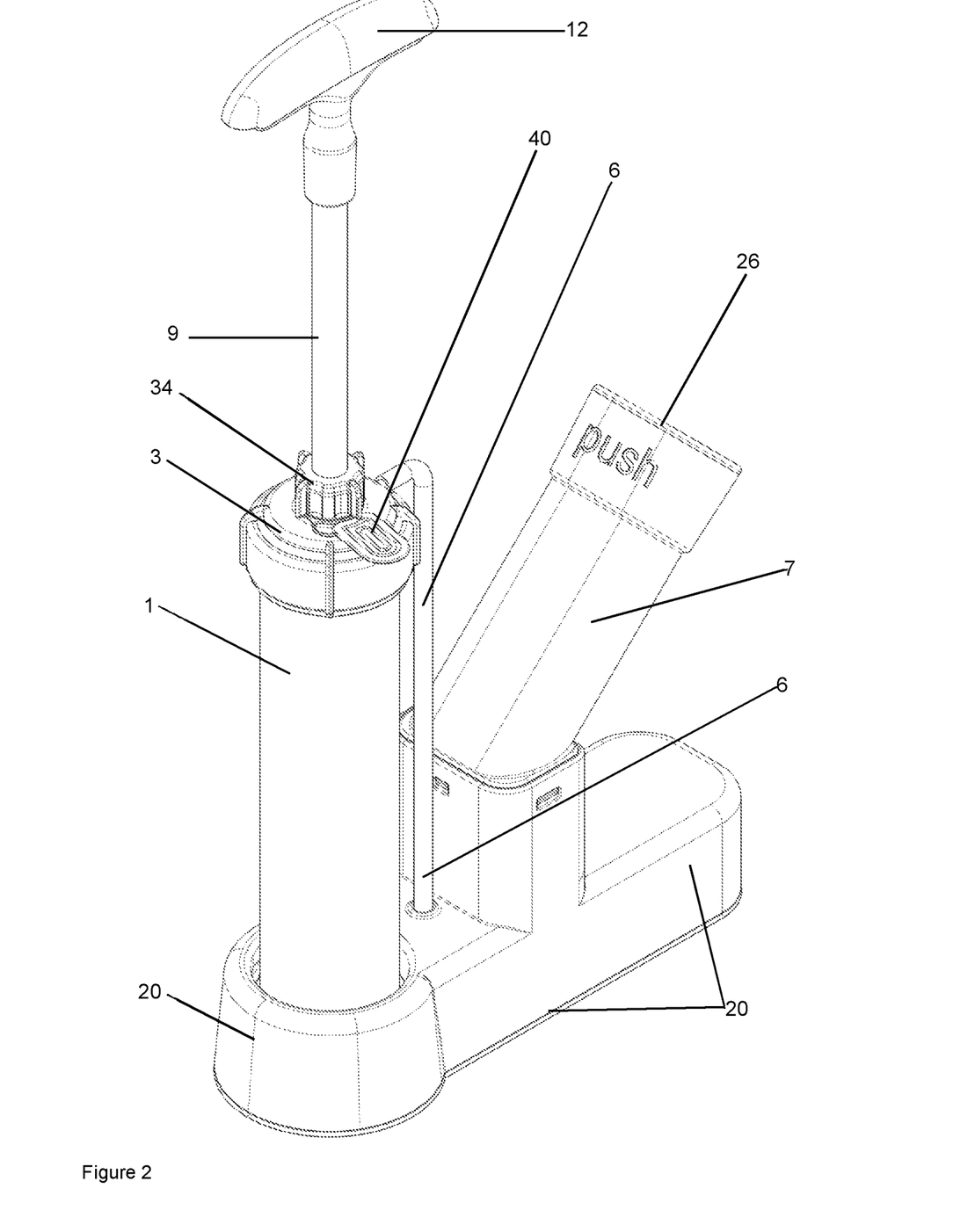
FIG. 2: a schematic perspective view of the storage and mixing device according to FIG. 1.
Figure 3:
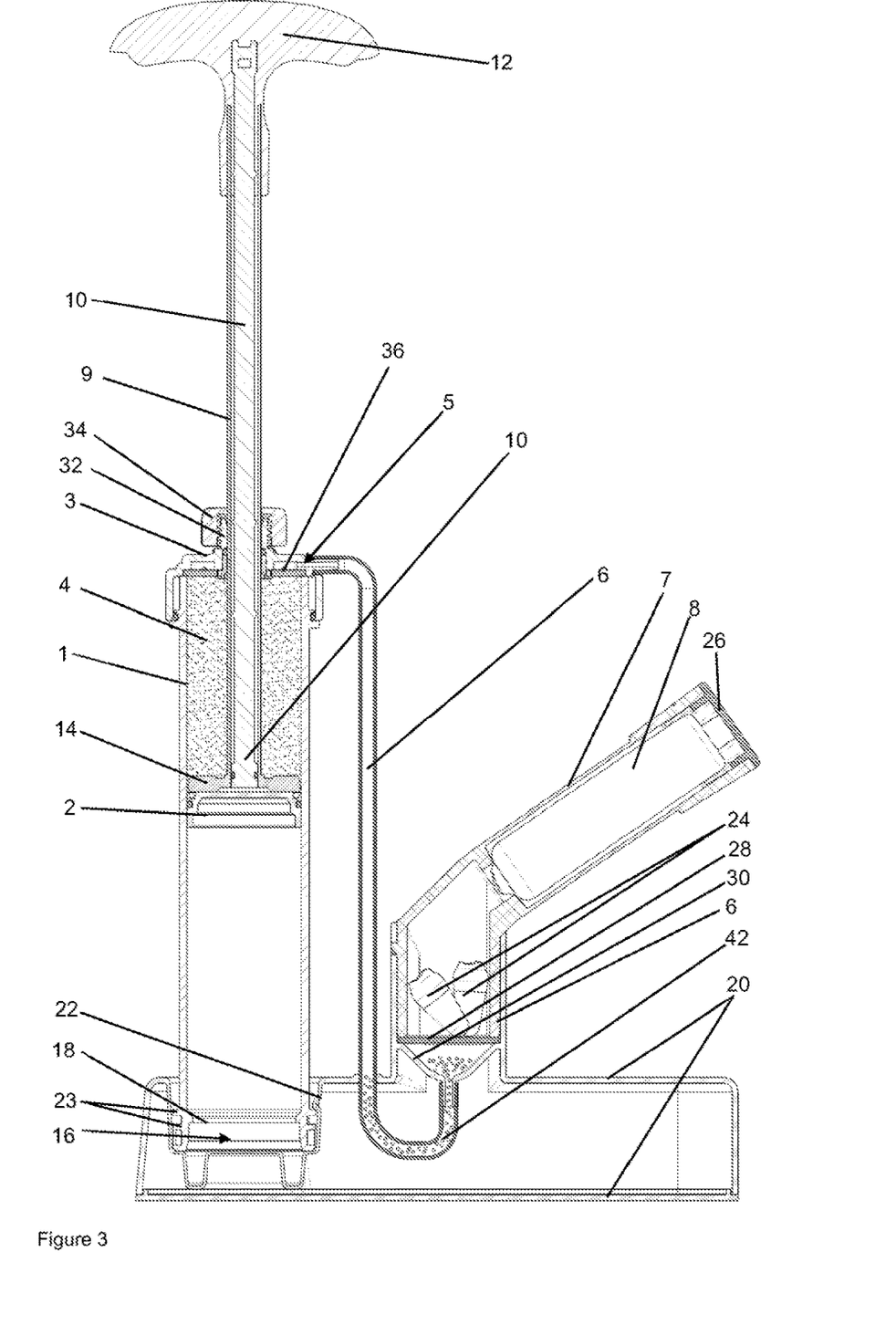
FIG. 3: a schematic cross-sectional view of the storage and mixing device where the monomer liquid container has been opened.
Figure 4:
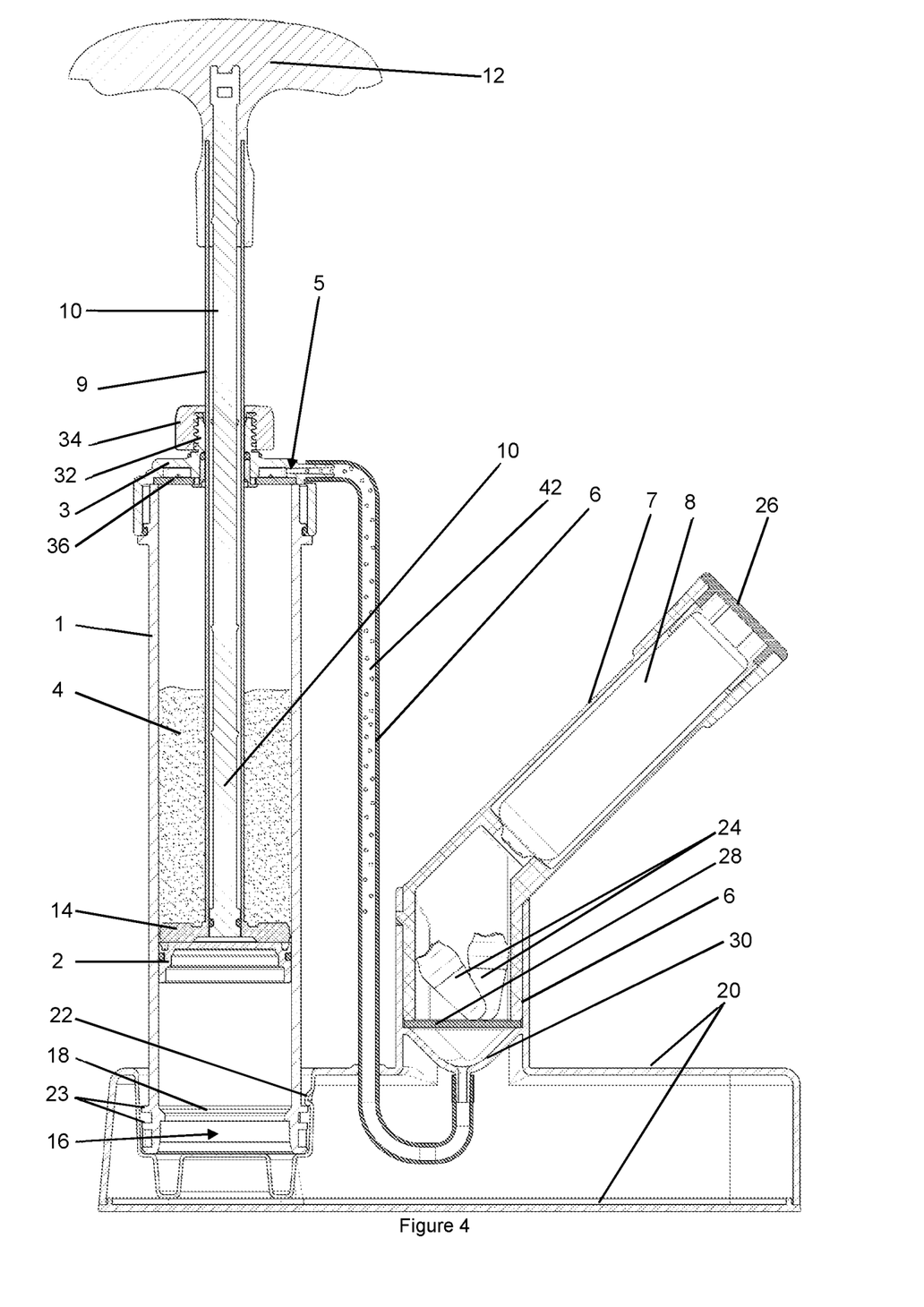
FIG. 4: a schematic cross-sectional view of the storage and mixing device during movement of the plunger to suck in the monomer liquid.
Figure 5:
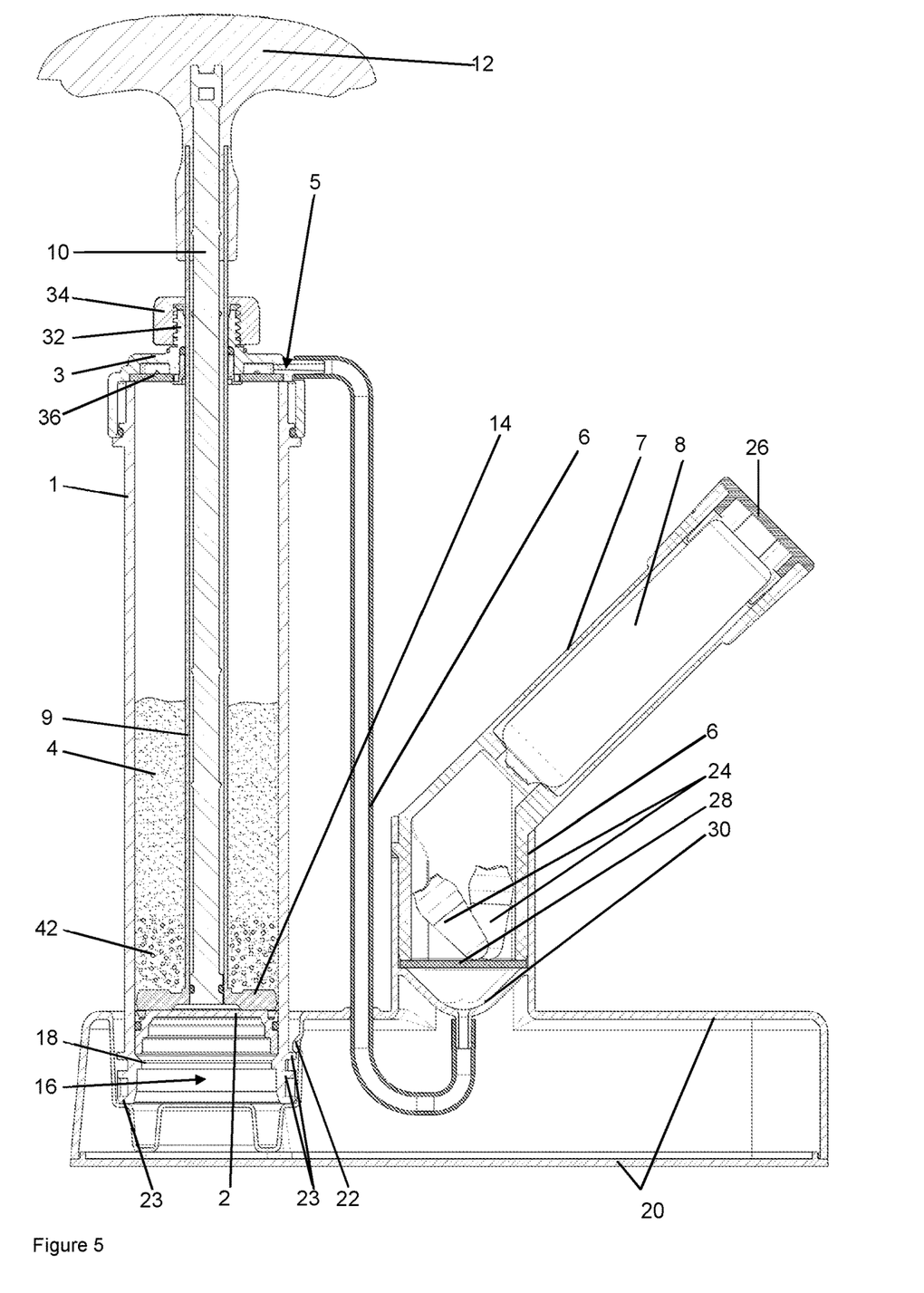
Figure 6:
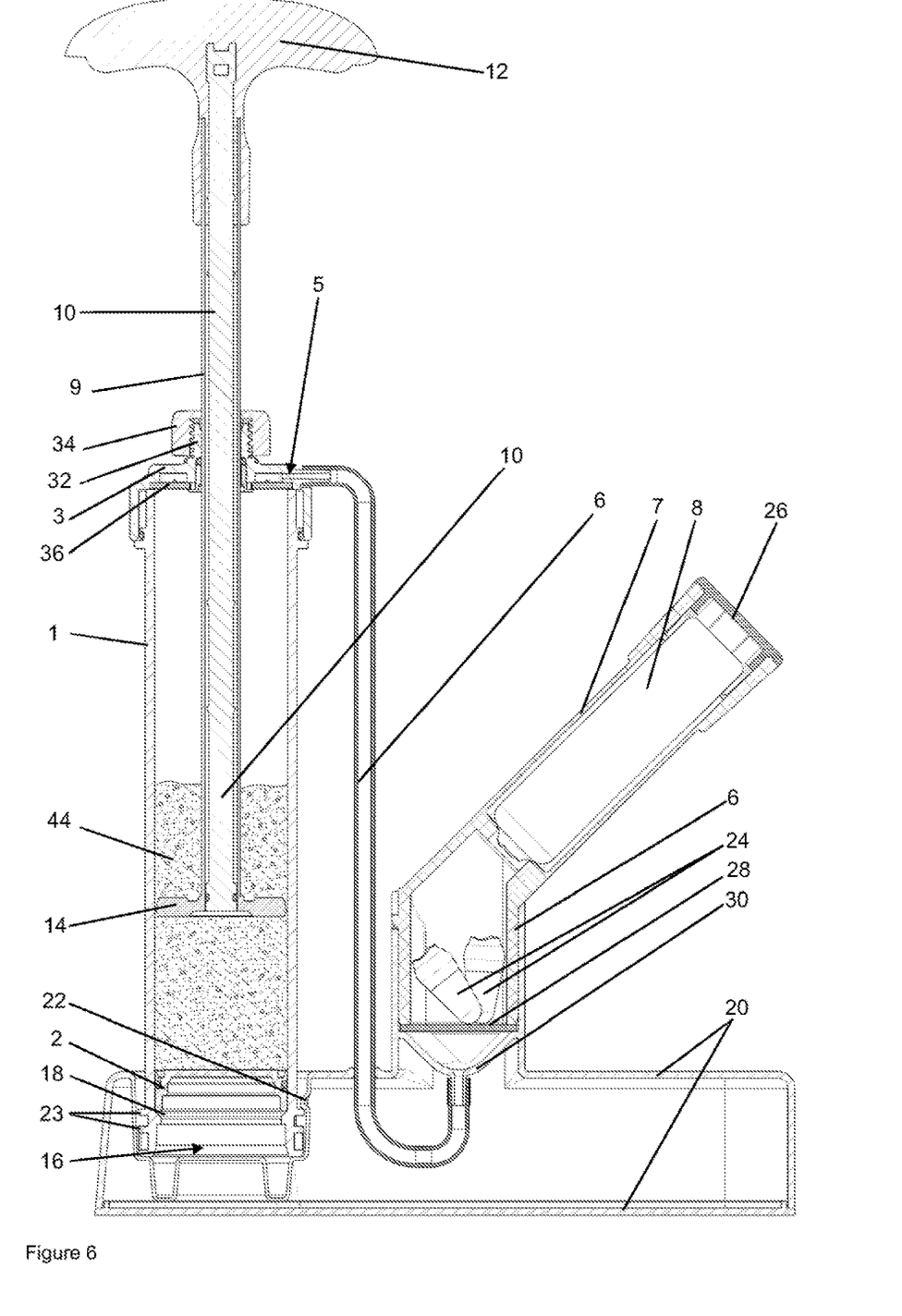
FIG. 6: a schematic cross-sectional view of the storage and mixing device where the bone cement paste has been mixed.
Figure 7:
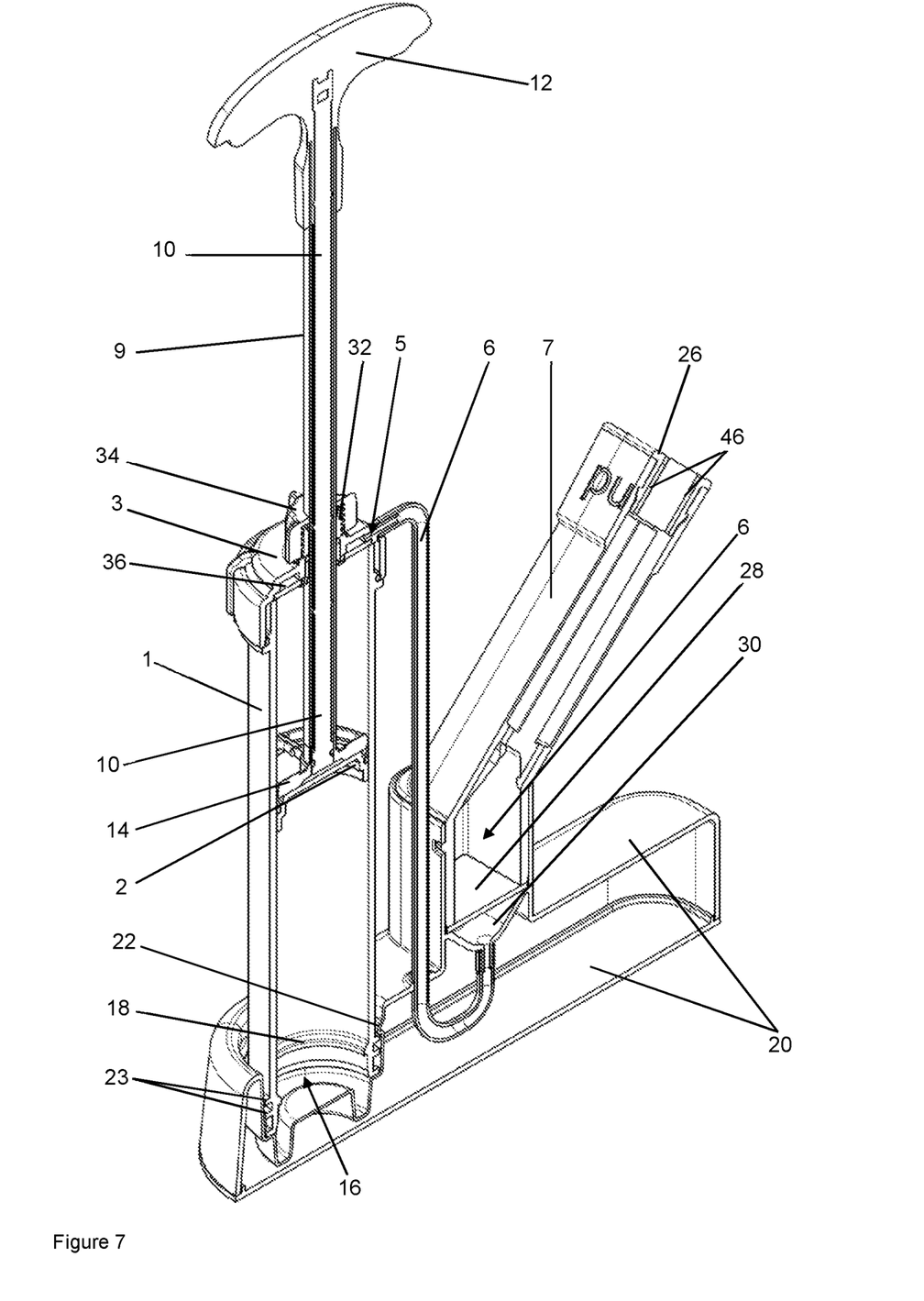
FIG. 7: a schematic perspective cross-sectional view of the storage and mixing device.
Figure 8:
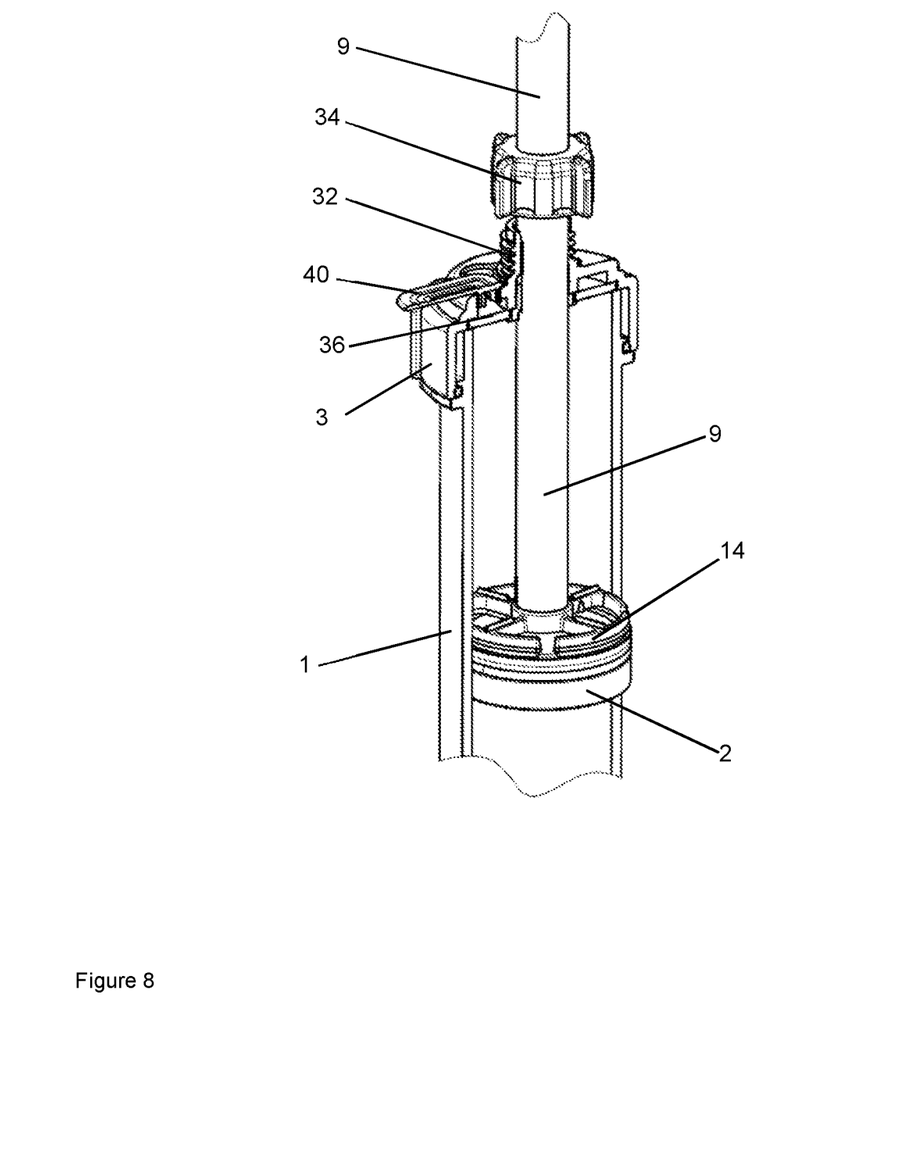
FIG. 8: a section of a schematic perspective partial cross-sectional view of the storage and mixing device.

FIGS. 1 to 6 are used below to describe an exemplary method according to the invention, which is carried out using the storage and mixing device according to the invention. The fully assembled storage and mixing device is provided, as shown in FIGS. 1 and 2. The glass ampoule 8 is opened by breaking off the ampoule head 24, so that the monomer liquid 42 flows out of the glass ampoule 8 into the widened region of the fluid line 6 and continues into the thin region of the fluid line 6 via the funnel 30. Here, fragments of the glass and the broken ampoule head 24 are retained by the screen 28 and/or the filter 28. The monomer liquid 42 from the glass ampoule 8 has now been filled into the fluid line 6 and is ready for use. This situation is shown in FIG. 3.

To transfer the monomer liquid 42 into the interior of the cartridge 1 and to produce a reduced pressure in the interior of the cartridge 1 in order to avoid gas inclusions in the bone cement paste 44 (see FIG. 6), the plunger 2 is pressed in the direction of the back side 16 of the cartridge 1 with the aid of the mixing rod 9. As a result, the volume between the plunger 2 and the cartridge head 3 in the interior of the cartridge 1 enlarges, so that a reduced pressure is produced. The reduced pressure sucks the monomer liquid 42 from the fluid line 6 in the direction of the cartridge 1 (see FIG. 4) and finally into the cartridge 1 (see FIG. 5) via the feed-through 5 and the porous filter 30. At the beginning (see FIG. 1), the plunger 2 is spaced from the back side 16 or the stop 18 to an extent that the total stroke of the plunger 2 to reach the stop 18 is sufficient to suck air out of the fluid line 6 as far as the monomer liquid 42 and to be able to suck the monomer liquid 42 into the interior of the cartridge 1.

The container 7 has openings 46 on the back side, for example in the lid 26, so that air can flow into the fluid line 6 from outside. However, the openings can as well be very small, so that they are not visible in the figures. In this case, however, there is no longer a reduced pressure in the interior of the cartridge 1 when the monomer liquid 42 has been sucked completely into the interior of the cartridge 1. Alternatively, a residual quantity of the monomer liquid 42 can also remain in the fluid line 6. If the structure is suitable, however, the gas pressure in the container 7 alone can be sufficient to press the monomer liquid 42 into the interior of the cartridge 1, so that openings in the container 7 are not required.

When the monomer liquid 42 has been sucked into the interior of the cartridge 1, it can be mixed with the bone cement powder 4 with the aid of the mixing device 14, by axially moving the mixing device 14 in the longitudinal direction and rotating it in the interior of the cartridge 1 manually with the aid of the mixing rod 9. In this way, the ready-mixed bone cement paste 44 (see FIG. 6) is produced. The mixing device 14 is then pulled towards the cartridge head 3 as far as the stop with the aid of the mixing rod 9, any securing device present (not shown) is removed and the mixing rod 9 is fixed relative to the cartridge head 3 by means of the sleeve nut 34. The core 10 is pulled out of the mixing rod 9 with the aid of the handle 12. The mixing rod 9 now forms a delivery pipe 9 which is arranged in the delivery opening or passes through the delivery opening and through which the ready-mixed bone cement paste 44 can be applied.

For this purpose, the cartridge 1 is separated from the foot part 20 by pulling it out and pulling the fluid line 6 off the feed-through 5. A one-way valve (not shown) can be provided in the fluid line in order to prevent the residual monomer liquid 42 from exiting the fluid line 6. The cartridge 1 is then inserted into a press-out device (not shown), by means of which the plunger 2 can be pressed in the direction of the cartridge head 3 as a delivery plunger 2 with the aid of an advanceable rod. In this way, the bone cement paste 44 is pressed out through the delivery pipe 9 and through the delivery opening. No bone cement paste 44 can escape through the feed-through 5 as the porous filter 36 holds back the bone cement paste 44.

The features of the invention disclosed in the above description, the claims, figures and exemplary embodiments can be relevant both individually and in combination for implementing the various embodiments of the invention.

LIST OF REFERENCE NUMERALS

1 Cartridge
2 Plunger
3 Cartridge head
4 Bone cement powder/first parent component
5 Feed-through
6 Fluid line
7 Container
8 Monomer liquid container/glass ampoule
9 Mixing rod/delivery pipe
10 Core
12 Handle
14 Mixing blade/mixing device
16 Back side of the cartridge/bottom side of the cartridge
18 Stop
20 Foot part
22 Latching nose
23 Projection
24 Ampoule head
26 Lid/plug
28 Screen/filter
30 Funnel
32 Fitting with outer thread
34 Conical sleeve nut/fastening device
36 Porous filter/porous disc
40 Closure
42 Monomer liquid
44 Mixed bone cement paste
46 Opening

The invention claimed is:

1. A storage and mixing device for two-component polymethyl methacrylate bone cements, said storage and mixing device comprising:

a cartridge with an interior, wherein the interior is delimited on a front side by a cartridge head with a closed delivery opening;

a plunger arranged to be axially movable in the interior of the cartridge and spaced from the cartridge head, wherein the plunger circumferentially rests against the inner wall of the interior, so that the plunger divides the interior of the cartridge into two sections in a gas-tight manner;

a powdery first parent component of the bone cement contained in the interior between the plunger and the cartridge head;

a container containing a monomer liquid as a second parent component of the bone cement;

a feed-through arranged in the cartridge head or in a cylinder barrel of the cartridge between the plunger and the cartridge head, wherein the feed-through is connected to a fluid line in which the monomer liquid is fillable or introducible;

a filter arranged in at least one of the cartridge head, the feed-through, and the fluid line, wherein the filter is permeable to the monomer liquid and impermeable to the powdery first parent component; and openings arranged in the container such that air is flowable through the openings into the fluid line from outside, wherein the plunger is spaced from a back side of the interior, located opposite the front side, to an extent that, by moving the plunger in the direction of the back side, a reduced pressure is producible in the interior of the cartridge between the plunger and the cartridge head, wherein the reduced pressure is able to suck the monomer liquid out of the fluid line into the interior of the cartridge.

2. The storage and mixing device according to claim 1, wherein the plunger in the interior of the cartridge is pushable or pullable manually in the direction of the back side of the interior by means of a rod or another force transmission means, so that a reduced pressure is produced in the interior of the cartridge between the plunger and the cartridge head.

3. The storage and mixing device according to claim 2, further comprising:

an actuating means or a handle affixed to the rod or the force transmission means.

4. The storage and mixing device according to claim 1, wherein the plunger is spaced from the back side of the interior such that the space for displacement of the plunger to reach the back side is at least equal to the volume of the monomer liquid to be sucked in.

5. The storage and mixing device according to claim 1, wherein the container is separated from the cartridge and connected or connectable to the fluid line.

6. The storage and mixing device according to claim 5, wherein the cartridge, the container and the fluid line are connected to a common stand, wherein the container and the fluid line are permanently connected to the stand and the cartridge is releasably connected to the stand.

7. The storage and mixing device according to claim 5, wherein a monomer liquid container, or a foil bag or a glass ampoule as the monomer liquid container, is contained in the container, which is openable within the container, so that the monomer liquid flows out of the opened monomer liquid container into the fluid line, wherein an opening device for opening the monomer liquid container, operable from outside, is arranged on the container.

8. The storage and mixing device according to claim 7, wherein the plunger is spaced from the back side of the interior such that the space for displacement of the plunger to reach the back side is at least equal to the volume of the fluid line and the monomer liquid container in which the monomer liquid is contained.

9. The storage and mixing device according to claim 1, wherein a mixing device is arranged in the interior of the cartridge between the plunger and the cartridge head, by means of which the first parent component is mixable with the monomer liquid in the interior of the cartridge.

10. The storage and mixing device according to claim 9, wherein the mixing device is operable from outside the cartridge by means of a mixing rod, wherein the mixing rod passes through the cartridge head in a gas-tight manner and is rotatable and movable in the axial direction.

11. The storage and mixing device according to claim 10, wherein the mixing rod passes through the delivery opening.

12. The storage and mixing device according to claim 10, wherein the plunger is pushable in the direction of the back side of the interior of the cartridge by means of the mixing rod.

13. The storage and mixing device according to claim 10, wherein the mixing rod is a delivery pipe in which a manually removable core is arranged, so that the mixed bone cement paste is dischargeable from the interior of the cartridge through the delivery pipe without the core.

14. The storage and mixing device according to claim 1, wherein, in the interior of the cartridge on the back side, a stop is provided which delimits movement of the plunger in the direction of the back side.

15. The storage and mixing device according to claim 1, wherein the plunger has at least one latching element which is releasably engageable with a complementary latching element on the inner side of the cartridge in the region of the back side of the interior.

16. The storage and mixing device according to claim 1, wherein a closable gas-permeable opening is arranged in the cartridge head, wherein a porous disc which is permeable to gases and impermeable to solid particles is arranged between the first parent component and the opening.

17. The storage and mixing device according to claim 16, wherein the porous disc is arranged in the cartridge head.

18. A method for mixing the parent components of a bone cement using the storage and mixing device according to claim 1, the method comprising:

a) preventing, via the filter, the powdery first parent component from making its way into the fluid line;

b) moving the plunger in the direction of the back side of the interior of the cartridge, wherein a reduced pressure is produced in the interior of the cartridge between the plunger and the cartridge head due to said movement of the plunger;

c) sucking the monomer liquid out of the fluid line and through the filter into the interior of the cartridge by the reduced pressure in the interior and flowing air through the openings in the container into the fluid line from the outside;

d) mixing the monomer liquid and the first parent component to form the bone cement paste in the interior of the cartridge; and e) discharging the bone cement paste from the interior of the cartridge through the delivery opening, that is opened, by advancing the plunger in the direction of the cartridge head.

19. The method according to claim 18, further comprising:

introducing the monomer liquid into the fluid line before b).

20. The method according to claim 19, wherein, after a monomer liquid container has been opened in the storage and mixing device, the monomer liquid is introduced into the fluid line.

21. The method according to claim 18, wherein, in b), the plunger is pressed in the direction of the back side of the cartridge by means of a mixing rod, wherein the mixing rod is movably supported in a gas-tight feed-through, in the delivery opening, in the cartridge head, and, in d), the monomer liquid is mixed with the first parent component by moving a mixing device, which is connected to the mixing rod, in the interior of the cartridge between the plunger and the cartridge head, by moving the mixing rod and therefore the mixing device.

22. The method according to claim 21, further comprising:
pulling the mixing device towards the cartridge head by means of the mixing rod and a core is removed from the mixing rod between d) and e), so that the mixing rod without the core forms a delivery pipe through which the mixed bone cement paste is pressed out of the interior of the cartridge in e).

23. The method according to claim 18, wherein, before e), the cartridge is separated from the storage and mixing device and inserted into a press-out device by means of which the plunger is pressed in the direction of the cartridge head in e), using a tappet or an advanceable rod, in order to discharge the bone cement paste from the interior of the cartridge.

24. The method according to claim 18, wherein the cartridge head is closed to be gas-tight before b).

25. A storage and mixing device for two-component polymethyl methacrylate bone cements, said storage and mixing device comprising:
a cartridge with an interior, wherein the interior is delimited on a front side by a cartridge head with a delivery opening;
a plunger arranged to be axially movable in the interior of the cartridge and spaced from the cartridge head, wherein the plunger circumferentially rests against the inner wall of the interior, so that the plunger divides the interior of the cartridge into two sections in a gas-tight manner;
a powdery first parent component of the bone cement contained in the interior between the plunger and the cartridge head;
a feed-through arranged in the cartridge head or in a cylinder barrel of the cartridge between the plunger and the cartridge head, wherein the feed-through is connected to a fluid line in which a monomer liquid as a second parent component of the bone cement is contained or into which a monomer liquid is fillable or introducible;
a filter arranged in at least one of the cartridge head, the feed-through, and the fluid line, wherein the filter is permeable to the monomer liquid and impermeable to the powdery first parent component; and
a mixing rod passing through the delivery opening of the cartridge head and having a mixing device affixed thereto in the interior of the cartridge between the plunger and the cartridge head, wherein mixing device is rotatable and axially movable in the interior of the cartridge such that the powdery first parent component is mixable with the monomer liquid in the interior of the cartridge,
wherein
the plunger is spaced from a back side of the interior, located opposite the front side, to an extent that, by moving the plunger in the direction of the back side, a reduced pressure is producible in the interior of the cartridge between the plunger and the cartridge head, wherein the reduced pressure is able to suck the monomer liquid out of the fluid line into the interior of the cartridge.

* * * * *